United States Patent [19]  
Beder et al.

[11] Patent Number: 4,479,865  
[45] Date of Patent: Oct. 30, 1984

[54] ELECTRODE ASSEMBLY

[75] Inventors: Alan H. Beder, Burlington, Mass.; Nai-Chiu J. Lai, Brookfield, Wis.

[73] Assignee: Ingold Electrodes, Andover, Mass.

[21] Appl. No.: 211,281

[22] Filed: Nov. 28, 1980

[51] Int. Cl.³ .............................................. G01N 27/30
[52] U.S. Cl. ................................................. 204/415
[58] Field of Search .................... 204/195 P, 1 P, 415; 128/635

[56] References Cited

U.S. PATENT DOCUMENTS

| | | | |
|---|---|---|---|
| 3,351,544 | 11/1967 | Medlar | 204/195 P |
| 3,649,505 | 3/1972 | Strickler et al. | 204/195 |
| 3,718,567 | 2/1973 | Haddad et al. | 204/195 P |
| 3,998,717 | 12/1976 | Watson et al. | 204/195 P |
| 4,175,028 | 11/1979 | Payton | 204/296 |
| 4,273,134 | 6/1981 | Ricciardelli | 128/635 |
| 4,280,505 | 7/1981 | Dali et al. | 128/635 |
| 4,303,076 | 12/1981 | Danek | 128/635 |

FOREIGN PATENT DOCUMENTS 1388339 3/1975 United Kingdom ............ 204/195 P
1388340 3/1975 United Kingdom ............ 204/195 P Primary Examiner—G. L. Kaplan

[57] ABSTRACT

A replaceable cap assembly for use with an electrochemical analysis electrode that includes an electrode body and an ion selective portion at an end of the body comprises a housing component for releasable attachment to the electrode body and a membrane securing component. The housing component has a cavity for receiving the ion selective portion when the housing is attached to the electrode body and a port in its end wall. A selectively permeable membrane that is disposed between two juxtaposed annular sealing elements extends across the port, and the membrane-annular sealing element assembly is fastened in place with the securing component such that the juxtaposed sealing members are compressed against the membrane to seal the port with the membrane being seated against the ion selective portion of the electrode when the cap assembly is attached to the electrode body.

14 Claims, 5 Drawing Figures

U.S. Patent  Oct. 30, 1984  4,479,865
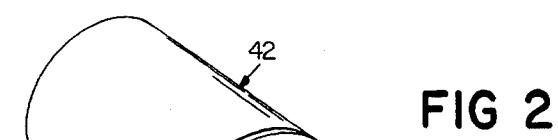
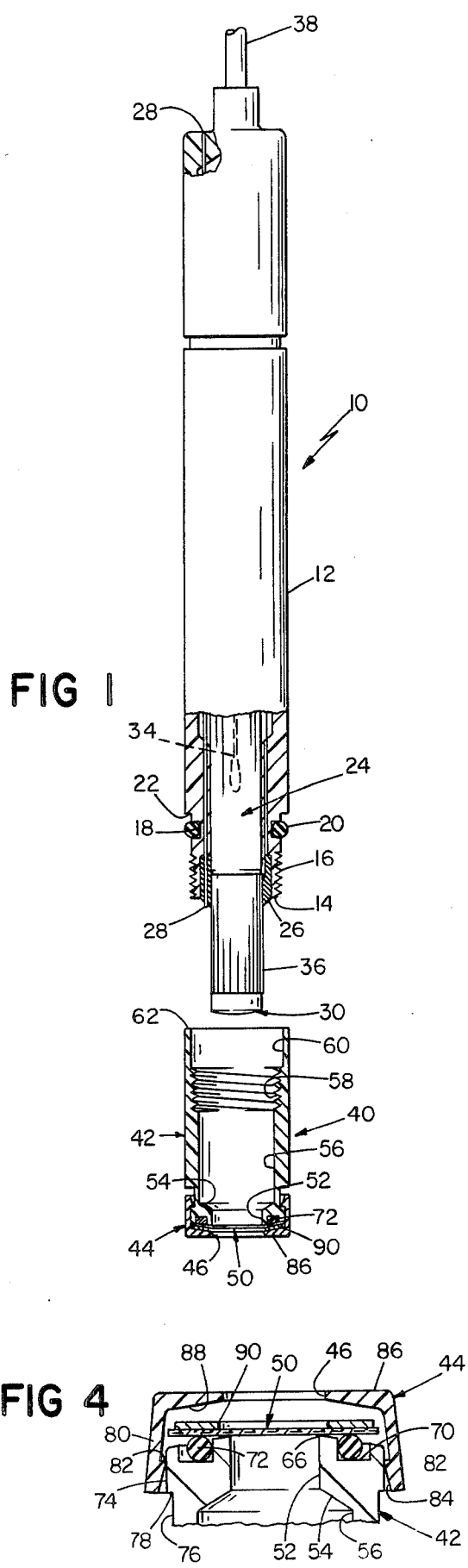
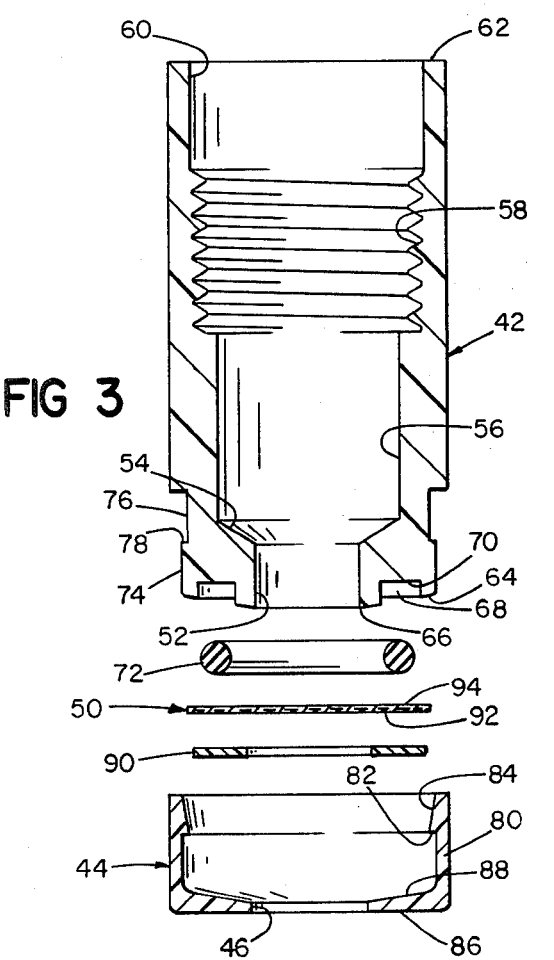
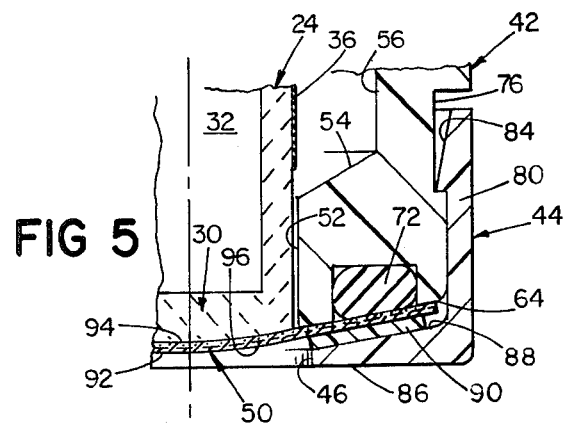

ELECTRODE ASSEMBLY

This invention relates to electrochemical electrode analysis systems and more particularly to electrode assemblies of the type that employ a selectively permeable membrane interposed between an electrode and the sample to be analyzed.

Such electrodes have been used for sensing a variety of gases including carbon dioxide and ammonia, in which the direct measurement of the gas is made potentiometrically through the use of an ion selective electrode assembly. For example, in the case of carbon dioxide, when the electrode assembly is exposed to a fluid containing carbon dioxide, the carbon dioxide diffuses across the permeable membrane in response to a partial pressure difference and equilibrates electrolyte confined between the permeable membrane and a hydrogen ion selective membrane, causing a change in hydrogen ion activity which is sensed by the electrode as a change in pH of the electrolyte such that the electrode develops a voltage related to $CO_2$.

The selectively permeable membrane and the internal fill solution are selected as a function of the type of gas to be sensed. A critical aspect is the permeable membrane-ion selective portion interface, and in many electrode constructions, it has been difficult to change or replace the membrane properly. A number of arrangements have been proposed to facilitate and simplify membrane replacement.

In accordance with the invention, there is provided a replaceable cap assembly for use with an electrochemical analysis electrode that includes an electrode body and an ion selective portion at an end of the body. The replaceable cap assembly comprises a housing component for releasable attachment to the electrode body, the housing component having a cavity for receiving the ion selective portion when the housing is attached to the electrode body and a port in the end wall of the housing. A selectively permeable membrane that is disposed between two juxtaposed annular sealing elements extends across the port, and the membrane-annular sealing element assembly is fastened in place with a securing component that has a clamp portion and latch structure for mechanical engagement with the housing component such that the clamp portion compresses the juxtaposed sealing members against the membrane to seal the port with the membrane being seated against the ion selective portion of the electrode when the cap assembly is attached to the electrode body. This electrode cap assembly provides a modular unit with a premounted selectively permeable membrane which provides consistent membrane alignment over the ion selective portion of the electrode, and ready conversion of the electrode to different gas sensitivities without direct handling of the membrane. The cap assembly eliminates "edge diffusion" effects at the membrane-sensor interface in an electrode system that is accurate and reliable and provides outputs of high sensitivity In preferred embodiments, the selectively permeable membrane is a composite structure that includes a layer of selectively permeable material in intimate contact with a porous layer that positions a film of electrolyte between the ion selective portion of the electrode and the selectively permeable layer. In particular embodiments, the selectively permeable layer is of microporous hydrophobic material (average pore size of about one micron or less) and the porous layer is of nonwoven hydrophilic material integrally attached to the hydrophobic layer.

In a particular embodiment, the end surface of the housing component is of conical configuration and the clamp portion has an annular surface of mating conical configuration. A first annular sealing element in the form of an O-ring is seated in a groove in the housing component and the second annular sealing element is an apertured disc of resilient material. A latch structure that fastens the securing component to the housing component includes a lead surface that terminates in an annular lip which seats in an annular groove in the housing component and is dimensioned so that the juxtaposed sealing members are both compressed; and the cap assembly is releasably attached to the electrode body by a thread arrangement.

Other features and advantages of the invention will be seen as the following description of a particular embodiment progresses, in conjunction with the drawing, in which:

FIG. 1 is a view, partially in section, of an electrode system in accordance with the invention;

FIG. 2 is a perspective view of the replaceable cap assembly of the system shown in FIG. 1;

FIG. 3 is an exploded view of components of the cap assembly;

FIG. 4 is a sectional view of portions of the cap assembly in partially interfitted relation; and FIG. 5 is an enlarged sectional view of a portion of the electrode system shown in FIG. 1 in assembled relation.

DESCRIPTION OF PARTICULAR EMBODIMENT

The gas sensing electrode assembly 10 shown in FIG. 1 includes a cylindrical probe body 12 that is about 1.6 centimeters in diameter and about 14 centimeters in length. Formed in end portion 14 of probe body 12 is a threaded section 16; an annular groove 18 which receives O-ring 20; and an annular cap stop surface 22. Disposed within body 12 is an elongated cylindrical glass tube 24 that has a diameter of about six millimeters and that is secured in body 12 by epoxy seal 26 through which vent tube 28 extends. An ion selective membrane 30 of pH sensitive glass is fused to the end of tube 24 and forms the lower wall of chamber 32. Disposed within tube 24 is a suitable electrolyte and a suitable conventional electrode 34. A reference electrode sleeve 36 is affixed on tube 24, and electrodes 34 and 36 are connected to shielded cable 38, for electrical connection to external measuring circuitry (not shown).

A replaceable cap assembly 40 includes body component 42 and clamp component 44. Port 46 in the end surface of clamp component 44 exposes membrane 50, as indicated in FIGS. 1 and 2.

Body component 42 is machined of chemical resistant polymeric material (e.g., black Delrin) and, as shown in the exploded view of FIG. 3, defines a cavity bounded by a series of stepped cylindrical surfaces: a bore 52 of about six millimeters diameter, a conical transition surface 54, a cylindrical surface 56 of about one centimeter diameter, a threaded section 58, and a cylindrical section 60 of about 1.3 centimeter diameter adjacent end surface 62. The lower surface 64 of body component 42 (opposite end surface 62) is of conical configuration and tapers at an angle of ten degrees outwardly from the edge 66 of bore 52. Annular recess 68 formed in end surface 64 has a radial width of about 2.5 millimeters and a base 70 recessed slightly less than 1.7 millimeters from end surface 66. Disposed in recess 68 is an O-ring 72 of about 1.7 millimeter diameter in cross-section, so that when O-ring 72 is seated in groove 68 in uncompressed condition, the surface of O-ring 72 protrudes slightly beyond the plane of end surface 66. Formed in the outer cylindrical surface 74 of body component 42 is a recess 76 that defines a radially extending latch surface 78 of about 0.3 millimeter in radial width.

Clamp component 44 is machined of chemical resistant polymeric material (e.g., black Delrin) and has an outer diameter of about 1.6 centimeters and a length of about 0.6 centimeter. Formed on the inner surface of cylindrical wall 80 is an annular latch lip 82 and a lead surface 84 that tapers at an angle of about five degrees. Extending inwardly from the lower end of wall 80 is an annular clamp flange 86 whose upper surface 88 is inclined at an angle of ten degrees and extends to port 46 that is about 6.5 millimeters in diameter. A silicone rubber disc 90 (about 0.3 millimeter in thickness) is arranged to seat on surface 88.

Disposed between O-ring 72 and seal disc 90 is a composite membrane 50 that has a selectively permeable outer layer 92 and a porous electrolyte film defining inner layer 94. The materials of composite membrane 50 are selected in accordance with the type of gas to be sensed. A membrane structure for use in an ammonia sensing system (for measuring ammonia, ammonium ion concentrations, and organic nitrogen following Kjeldahl digestion) includes an outer layer 92 of microporous hydrophobic (expanded polytetrafluoroethylene) film that has an average pore diameter of about one micron and an inner layer 94 of porous (nonwoven polyester) hydrophilic material, the composite membrane having a porosity of about 91 percent and a nominal thickness of about 0.2 millimeter and being obtainable from W. L. Gore and Associates, Inc., under the tradename "GORE-TEX". A composite membrane structure for use in a nitrogen oxide sensing system (for measuring nitrite, nitrate, and nitrogen oxide) includes an outer layer 92 of microporous hydrophobic expanded polytetrafluoroethylene film of 0.5 micron pore size secured in intimate contact to a hydrophilic (nonwoven polyester) inner layer 94 to provide a similar membrane of about 0.2 millimeter thickness that has a porosity of about 84 percent. A composite membrane for measurement of carbon dioxide, carbonates and bicarbonates includes a selectively permeable outer layer 92 of silicone rubber and a nylon mesh inner layer 94.

In assembly of the replaceable structure 40, body component 42 is inverted, as shown in FIG. 4, and O-ring 72 is seated in groove 68. Composite membrane 50 is then positioned on O-ring 72 and seal disc 90 on membrane 50. Clamp component 44 is then slid axially over component 42 with lead surface 84 sliding along body surface 74 until latch surface 82 snaps over on cooperating surface 78. As clamp surface 88 moves towards body surface 64, it rolls the peripheral margin of seal disc 90 and membrane 50 on O-ring 72 in a radial tensioning of membrane 50 and then seal disc 90 and O-ring 72 are compressed against the interposed composite membrane 50. As indicated above, both seal disc 90 and composite membrane 50 each have a thickness of about 0.2 millimeter such that, with clamp component 44 secured to body component 42 by the interference snap fit, juxtaposed sealing elements 72 and 90 are both compressed and provide excellent sealing of the tensioned membrane 50. The assembled cap unit firmly supports membrane 50.

In use, the appropriate internal fill solution is placed in cap 44 and glass tube 24 is inserted through bore 52 and threads 16 and 58 are engaged to seat cap end surface 62 against body reference surface 22. In this position, the end surface 96 of pH glass membrane 30 (which is a smoothly curved convex surface that has a rim to center height of about 0.3 millimeter) is seated against membrane 50, as indicated in FIG. 5, slightly bowing the tensioned membrane so that the entire membrane surface 96 contacts the inner layer 94 of membrane 50 which provides a uniform thickness of electrolyte at surface 96 of glass membrane 30.

The replaceable electrode cap 40 provides a premounted selectively permeable membrane in a modular assembly that accommodates different membrane materials and assures consistent membrane alignment over the end surface of glass membrane 30 in an arrangement which protects the hydrophobic characteristics of the membrane, eliminates "edge diffusion" effects at the membrane-sensor interface and facilitates changing of membranes for measurement of different gases.

While a particular embodiment of the invention has been shown and described, various modifications will be apparent to those skilled in the art and therefore it is not intended that the invention be limited to the disclosed embodiment or to details thereof, and departures may be made therefrom within the spirit and scope of the invention.

What is claimed is:

1. A Replaceable cap assembly for use with an electrochemical analysis electrode that includes an electrode body and an ion selective portion at an end of said body, said replaceable cap assembly comprising a housing component for releasable attachment to said electrode body, said housing component having a cavity for receiving said ion selective portion when said housing component is attached to said electrode body and an end wall surface of conical shape that defines a port in communication with said cavity, said conical end wall surface surrounding and sloping away from said port, an annular groove in said concial end wall surface, a first annular sealing element of O-ring type disposed in said groove in coaxial relation to said port, a selectively permeable membrane seated on said first sealing element and extending across said port, a second annular, disc type sealing element seated on said membrane in juxtaposed relation to said first sealing element, a membrane securing component having a clamp portion that includes an inwardly extending annular flange that has a conical inner surface of mating configuration to said conical end wall surface, and snap action latch structure axially movable between released and latched positions, said latch structure in said latched position being in mechanical engagement with said housing component with said conical surface of said clamp portion compressing said juxtaposed first and second annular sealing elements against said membrane and placing said membrane in radial tension to seal said port, said membrane being seated against said ion selective portion when said cap assembly is attached to said electrode body.

2. The assembly of claim 1 wherein said latch structure includes an annular groove and cooperating annular latch lip structure.

3. The assembly of claim 1 wherein said membrane is a composite of a microporous hydrophobic layer and a porous hydrophilic layer in contact with said hydrophobic layer, said hydrophilic layer being seated against said conical end wall surface of said housing component.

4. The assembly of claim 3 wherein said hydrophobic layer is composed of microporous polytetrafluoroethylene that has an average pore size of about one micron or less.

5. The assembly of claim 4 wherein said porous hydrophilic layer is of nonwoven polyester fibers fused to said hydrophobic layer.

6. The assembly of claim 1 wherein said housing component has screw threads for attachment to cooperating threads of said electrode body.

7. A replaceable cap assembly for use with an electrochemical analysis electrode that includes an electrode body and an ion selective portion at an end of said body,
said replaceable cap assembly comprising
a housing component for releasable attachment to said electrode body, said housing component having a cavity for receiving said ion selective portion when said housing component is attached to said electrode body and a port in the end wall of said housing component, said end wall having a conical outer surface that surrounds and slopes away from said port, an annular groove in said conical outer surface, a first annular sealing element of O-ring type disposed in said groove in coaxial relation to said port, a second annular, disc type sealing element in juxtaposed relation to said first sealing element and overlying said conical outer surface,
a selectively permeable membrane interposed between said first and second sealing elements and extending across said port,
a membrane securing component having a clamp portion, said securing component clamp portion including an inwardly extending annular flange portion that has a conical inner surface of mating configuration to the conical outer surface of said housing portion, and latch structure in mechanical engagement with said housing component such that said conical inner surface of said clamp portion compresses said juxtaposed first and second annular sealing members against said conical end surface of said housing portion and said membrane is in radial tension to seal said port, said membrane being seated against said ion selective portion when said cap assembly is attached to said electrode body.

8. The assembly of claim 7 wherein said membrane is a composite of a microporous hydrophobic layer and a porous hydrophilic layer in contact with said hydrophobic layer, said hydrophilic layer being seated against said conical end wall surface of said housing component.

9. The assembly of claim 8 wherein said hydrophobic layer is composed of microporous polytetrafluoroethylene that has an average pore size of about one micron or less, and said porous hydrophilic layer is of nonwoven polyester fibers fused to said hydrophobic layer.

10. The assembly of either claim 1 or 9 wherein said clamp portion has a circular opening of larger diameter than said housing component port.

11. A replaceable cap assembly for use with an electrochemical analysis electrode that includes an electrode body and an ion selective portion at an end of said body,
said replaceable cap assembly comprising
a housing component for releasable attachment to said electrode body, said housing component having a cavity for receiving said ion selective portion when said housing component is attached to said electrode body, an end wall surface of conical configuration, and a port in said conical end wall surface,
first and second juxtaposed annular sealing elements in coaxial relation to said port, said second sealing member overlying said conical end wall surface,
a composite selectively permeable membrane interposed between said first and second sealing elements and extending across said port, said composite membrane having a micoporous hydrophobic layer and a porous hydrophilic layer fused to said hydrophobic layer,
a membrane securing component having a clamp portion that includes an inwardly extending flange portion that has a conical inner surface of mating configuration to said conical end wall surface, and snap action latch structure mechanically coupling said securing and housing components together, said latch structure being axially movable between released and latched positions with said latch structure in latched position holding said securing and housing components such that said conical inner surface of said flange portion overlies and compresses said first and second sealing elements against said composite membrane between said juxtaposed first and second annular sealing elements to seal said port and said membrane is in radial tension, said hydrophilic layer of said composite membrane being seated against said ion selective portion when said cap assembly is attached to said electrode body.

12. The assembly of claim 11 wherein said mechanical coupling structure includes recess and cooperating latch lip structure.

13. The assembly of claim 12 wherein said first annular sealing element is an O-ring and said second annular seal element is an apertured disc of resilient material, said latch structure includes an annular groove and cooperating annular latch lip structure, and said housing component has screw threads for attachment to cooperating threads of said electrode body.

14. The assembly of claim 11 wherein said hydrophobic layer is composed of microporous polytetrafluoroethylene that has an average pore size of about one micron or less, and said porous hydrophilic layer is of nonwoven polyester fibers fused to said hydrophobic layer.

* * * * *